(12) United States Patent
Burek

(10) Patent No.: US 6,361,532 B1
(45) Date of Patent: *Mar. 26, 2002

(54) ELECTROSURGICAL PENCIL

(75) Inventor: Paul P. Burek, Aurora, CO (US)

(73) Assignee: Bovie Medical Corporation, St. Petersburg, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/637,927

(22) Filed: May 1, 1996

(51) Int. Cl.[7] ............................................. A61B 18/18
(52) U.S. Cl. ........................................ 606/45; 606/49
(58) Field of Search .................... 606/32, 34, 40, 606/41, 42, 45, 49, 50, 37; 607/115, 116, 145, 146

(56) References Cited

U.S. PATENT DOCUMENTS

| | | | |
|---|---|---|---|
| 2,888,928 A | * 6/1959 | Seiger | 606/49 |
| 3,801,766 A | 4/1974 | Morrison, Jr. | 200/157 |
| 4,032,738 A | 6/1977 | Esty et al. | 200/157 |
| 4,034,761 A | 7/1977 | Prater et al. | |
| 4,427,006 A | 1/1984 | Nottke | |
| 4,492,832 A | 1/1985 | Taylor | 200/52 R |
| 4,545,375 A | 10/1985 | Cline | |
| 4,562,838 A | 1/1986 | Walker | |
| 4,619,258 A | 10/1986 | Pool | |
| 4,625,723 A | * 12/1986 | Altnether et al. | 606/42 |
| 4,688,569 A | 8/1987 | Rabinowitz | |
| 4,754,754 A | * 7/1988 | Garito et al. | 606/45 |
| 4,802,476 A | 2/1989 | Noerenberg et al. | |
| 4,922,903 A | 5/1990 | Welch et al. | 606/37 |
| 5,000,754 A | 3/1991 | DeOliveira et al. | 606/42 |
| 5,013,312 A | 5/1991 | Parins et al. | 606/37 |
| 5,226,904 A | 7/1993 | Gentelia et al. | 606/42 |
| 5,256,138 A | 10/1993 | Burek et al. | 606/42 |
| 5,376,089 A | 12/1994 | Smith | 606/42 |
| 5,484,434 A | 1/1996 | Cartmell et al. | 606/37 |
| 5,630,812 A | * 5/1997 | Ellman et al. | 606/45 |
| 5,643,296 A | * 7/1997 | Hundertmark et al. | 604/22 |

* cited by examiner

Primary Examiner—Linda C. M. Dvorak
Assistant Examiner—R. Kearney
(74) Attorney, Agent, or Firm—Webb Ziesenheim Logsdon Orkin & Hanson, P.C.

(57) ABSTRACT

An electrosurgical pencil for delivering high frequency cutting and coagulation signals from an electrosurgical generator is disclosed. A flexible, elongated, substantially solid pencil housing is provided having a cable receiving end and a blade electrode receiving end opposed from the cable receiving end. A mechanism is provided within the pencil housing for bending of the pencil housing between the cable receiving end and the blade electrode receiving end. Additionally, a mechanism is provided within the electrosurgical pencil for retaining a bent position of the pencil housing. The electrosurgical pencil of the present design may be a foot controlled electrosurgical pencil or may include a manually actuated switch within the pencil housing to form a hand controlled electrosurgical pencil.

19 Claims, 3 Drawing Sheets

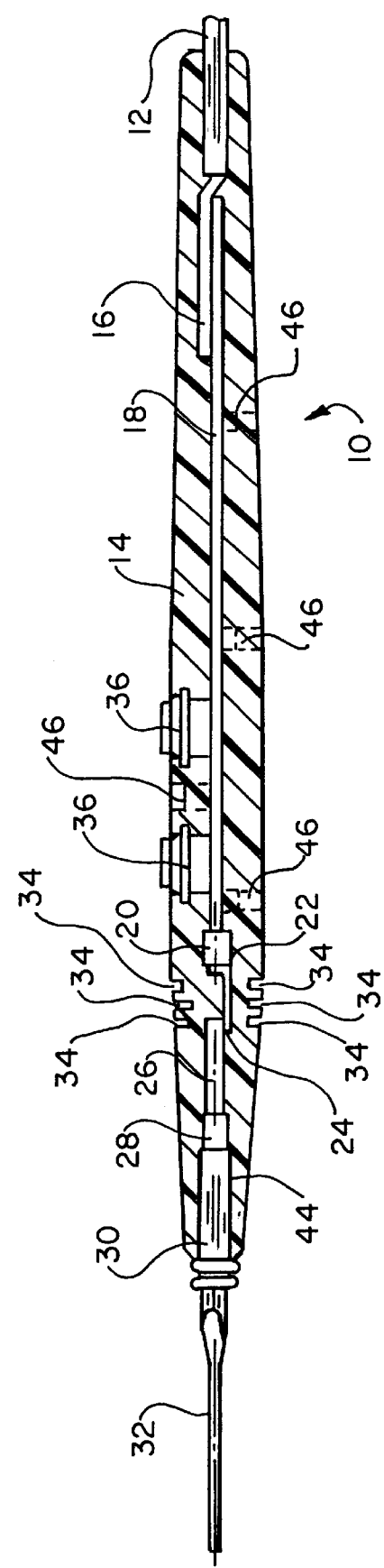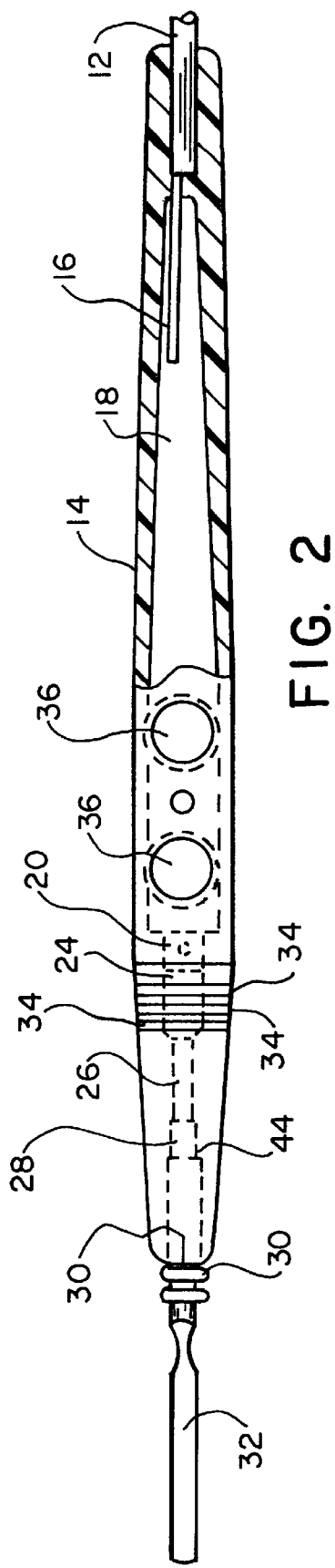

ELECTROSURGICAL PENCIL

BACKGROUND OF THE INVENTION

1. Field of the Invention

The present invention relates to electrosurgical hand controlled and foot controlled pencils. More specifically, the present invention relates to an electrosurgical pencil having a flexible, substantially solid pencil housing.

2. Prior Art

In electrosurgical techniques using electrosurgical pencils, an electrosurgical generator generates current in a particular wave form upon demand, and the current is carried to an electrosurgical pencil having a relatively small blade. The current is transmitted through the blade to the patient and back to the generator through a ground plate attached to the patient. Since the blade is relatively small relative to the ground plate, the energy being transferred to the patient through the small blade is concentrated such that the high frequency causes tissue destruction. Typically, such devices have two modes of operation, cutting and coagulation, which require current having different wave forms.

In hand controlled electrosurgical pencils, an internal switch, usually a printed circuit board, is incorporated into the pencil housing. The housing additionally includes appropriate buttons to select the desired mode of operation through the printed circuit board (i.e., either a cutting or coagulation signal). In electrosurgical pencils without hand actuations, often called foot controlled pencils, an actuation switch is positioned remote from the pencil housing to be controlled by another manner such as by the operator's foot.

In both the hand controlled and foot controlled electrosurgical pencils, the pencil housing is intended to form a barrier to prevent fluid entry therein. The pencil housings of the prior art are generally formed of two hollow, rigid plastic parts that are joined together by ultrasonic welding. The hollow configuration, ultrasonic welding and the rigid construction of the prior art pencils all provide for a series of problems. The use of an ultrasonic assembly for ultrasonic welding may still leave voids between the two housing parts and compromise the hermetic seal provided. Additionally, the rigid plastic housing does not provide any stress relief for the cable which connects the pencil housing to the electrosurgical generator. Consequently, the rigid plastic housings increase the likelihood of a break in the cable (i.e., wire fatigue) at the point where the cable enters the pencil housing. A further problem with the prior art housings is that they do not accommodate changes in the blade positioning. For example, users sometimes bend the blade of the blade electrode to more effectively reach the operating position. However, the bending of the blade itself is undesirable since the blade can reach relatively high temperatures, and touching the blade itself can be dangerous to the user and may contaminate the electrosurgical pencil.

SUMMARY OF THE INVENTION

An object of the present invention is to overcome the drawbacks of the prior art electrosurgical pencils. A further object of the present invention is to provide an electrosurgical pencil providing a substantially electrically insulated housing hermetically sealing the interior to provide a more effective insulated barrier to the external environment. A further object of the present invention is to provide an electrosurgical pencil which can be easily manipulated to the desired operating configuration. A further object of the present invention is to provide an electrosurgical pencil which is efficient and economic to manufacture.

Many of the objects of the present invention are achieved by providing an electrosurgical pencil for delivering high frequency cutting and coagulation signals from an electrosurgical generator with the pencil including a flexible, elongated pencil housing having a cable receiving end and a blade electrode receiving end opposed from the cable receiving end. The pencil housing is provided with a mechanism for permitting bending of the pencil housing between the cable receiving end and the blade electrode receiving end. Further objects of the present invention are achieved by providing that the housing is formed of an elastomeric polymer which is sealed around a portion of the collet and around a portion of the cable forming a substantially solid housing therebetween.

The present invention additionally discloses a method for manufacturing an electrosurgical pencil to achieve the above objects. The method according to the present invention includes the steps of encapsulating the elongated elastomeric pencil housing around a portion of the cable and around a portion of the collet to form the substantially solid housing therebetween. The electrically insulated solid housing substantially completely encapsulates the interior mechanisms of the electrosurgical pencil, thereby creating a hermetic seal and offering a seamless, insulated barrier to the external environment. An insert molding process provides for an efficient and effective method for manufacturing the electrosurgical pencil of the present design.

In one embodiment of the present invention, the mechanism for permitting bending includes a plurality of parallel grooves on opposite sides of the pencil housing. One embodiment of the present invention additionally includes a metal collet positioned within the pencil housing wherein the metal collet is bendable with the pencil housing and the metal collet maintains a bent position of the pencil housing. The metal collet may include a bendable flat portion with a round electrode receiving socket attached to the flat portion for rotatably receiving a blade electrode therein through a blade electrode receiving end of the pencil housing. The pencil housing may be hermetically sealed around a flat portion of the metal collet.

A hand controlled embodiment of the present invention provides a manually actuated switch embedded within the pencil housing between the collet and the cable with both the collet and the cable attached to the switch. The switch may have a rigid switch body to provide rigidity to the elastomeric pencil housing of the electrosurgical pencil. The rigid switch body may be spaced from the cable receiving end of the pencil housing wherein the pencil housing tapers from the end of the switch body to the cable receiving end. Additionally, at least one button may be provided on the pencil housing with each button overlaying a depressible activation member on the switch wherein the housing includes an encapsulating membrane over the activation member between the button and the activation member.

These and other objects of the present invention will be clarified in the description of the preferred embodiment wherein like reference numerals represent like characters throughout.

BRIEF DESCRIPTION OF THE DRAWINGS

FIG. 1 is a cross-sectional side view of an electrosurgical pencil according to the present invention;

FIG. 2 is a plan view, partially in section, of the electrosurgical pencil illustrated in FIG. 1;

BRIEF DESCRIPTION OF THE PREFERRED EMBODIMENT

FIGS. 1–6 illustrate a hand controlled electrosurgical pencil 10 according to the present invention. The pencil 10 includes an insulated cable 12 which is connectable with an electrosurgical generator (not shown) in a known manner such as with a three-prong plug. The cable 12 is received within a first end of a pencil housing 14 as best shown in FIGS. 1 and 2. Leads 16, shown schematically in FIGS. 1 and 2, of the cable 12 are attached to appropriate portions of a printed circuit board switch 18. The switch 18 is preferably formed with a rigid body to provide a certain amount of rigidity to the pencil housing 14 as will be described hereinafter.

Figure 4:
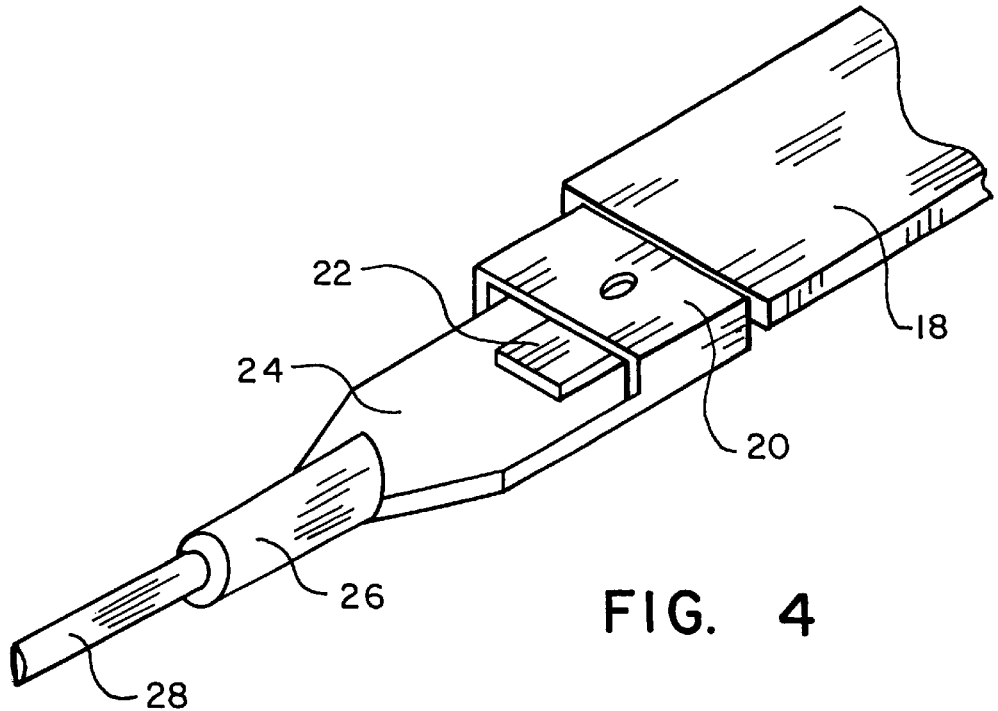
FIG. 4 is an enlarged view of a collet of the electrosurgical pencil shown in FIGS. 1 and 2 with the pencil housing removed for clarity.

An attachment end 20 of a metal collet is crimped or otherwise secured to a lead 22 of the switch 18. This connection is schematically illustrated in FIG. 4. The metal collet includes a flat portion 24 extending from the attachment end 20 to a cylindrical blade electrode receiving socket 26.

A round connecting lead 28 of a blade electrode is rotatably received within the socket 26. The blade electrode additionally includes a surrounding plastic sleeve 30 positioned between the connecting lead 28 and the operative blade 32 of the blade electrode. Blade electrodes conventionally come in a variety of lengths and shapes for operative blade 32.

Figure 3:
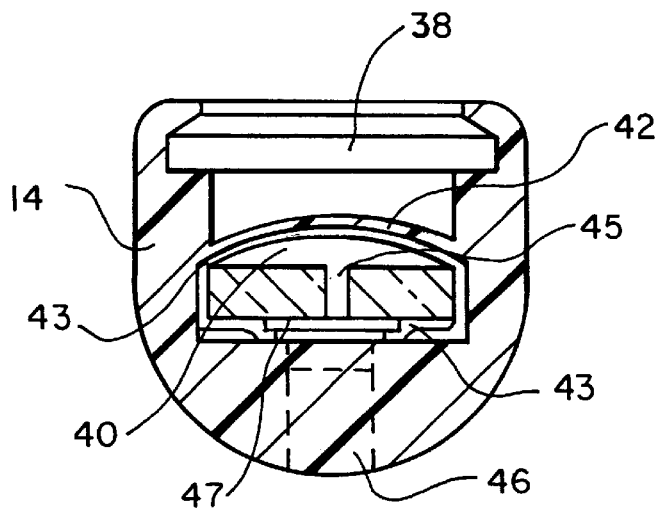
FIG. 3 is an enlarged sectional view of the button holding assembly of the pencil housing illustrated in FIGS. 1 and 2 with the button removed for clarity.

A plurality of parallel, aligned relief grooves 34 is positioned on opposed sides of the pencil housing 14. Additionally, the pencil 10 includes a pair of actuation pegs or buttons 36 held in button recesses 38 formed in the pencil housing 14 as shown in FIG. 3. In FIG. 3, the button 36 has been removed for clarity. As schematically illustrated in FIG. 3, the printed circuit board switch 18 includes a pair of dome switches 40 which are actuated by pressing the dome as is known in the art. The dome switches 40 are illustrated in an exaggerated manner in FIG. 3. As shown in FIG. 3, the recesses 38 and corresponding button 36 overlay the dome switches 40. Additionally, the pencil housing 14 includes a thin film or membrane 42 overlaying the dome switches 40 between the buttons 36 and dome switches 40.

In the manufacturing process, the dome switches 40 are held in place by nonconductive, high voltage resistant tape 43. The tape 43 secures each dome switch 40 in place against the printed circuit board switch 18, preventing the molten elastomeric polymer from entering the underside of the dome switch 40 during manufacturing. The tape 43 provides additional electrical insulation to the pencil 10 and further assists in the encapsulation of the interior of the pencil 10 by the pencil housing 14.

The printed circuit board switch 18 includes one or more pilot holes 45 extending to the dome switches 40. The pilot holes 45 become important for easy, effective operation of the dome switches 40 due to the encapsulation of the printed circuit board switch 18 by the housing 14. Without the pilot holes 45, the encapsulation of the printed circuit board switch 18 would make the dome switches 40 very difficult to depress to the very small, confined gas bubble defined by each dome switch 40.

A cover or tape 47 is placed over the pilot holes 45 to prevent the molten elastomeric polymer from entering the pilot holes 45. The tape 47 only requires a sufficient tensile strength to prevent the molten polymer from entering and filling the pilot holes 45 and, therefore, may be difficult from the nonconductive, high voltage tape 43 which holds the dome switches 40 in place. However, if a single tape member can provide the nonconductive, high voltage criteria required for tape 43 and the tensile strength required by tape 47, then the single tape member could be used. The single tape member would be wrapped completely around the printed circuit board switch 18 in place of separate tape elements 43 and 47.

The end of the pencil housing 14 opposed from the cable receiving end includes an aperture 44 extending from the end of the pencil housing 14 to the socket 26 of the metal collet. The aperture 44 is sized to frictionally engage the sleeve 30 of the blade electrode to more securely receive the blade electrode therein.

The housing 14 is sealed around the flat portion 24 of the metal collet and around the cable 12 at the first end of pencil housing 14 and is substantially solid therebetween. The pencil housing 14 completely encapsulates the printed circuit board switch 18 by including membranes 42 over the dome switches 40. In pencils 10 using high durometer hardness plastic, the membranes 42 would be eliminated, and the tape 43 would act as an encapsulating membrane for the pencil housing 14 with the pencil housing 14 firmly attached and sealed to the tape 43. The sealing around the flat portion 24 and around the cable 12 with the substantially solid pencil housing 14 therebetween, which substantially completely encapsulates the switch 18, provides a more effective barrier to prevent fluid entry than previously provided in the prior art. The pencil housing 14 can be formed by insert molding techniques using an elastomeric, nonconductive polymer. In the insert molding techniques, holding pins will be utilized to position the switch 18 which results in a plurality of pin holes 46. An important aspect of the present invention is that in the final molded pencil housing 14 the pin holes 46 do not extend all the way to the switch 18 as shown in FIGS. 1 and 2 such that the pencil housing 14 substantially completely encapsulates the switch 18, preventing the sealed environment from being compromised. During manufacture, the holding pins are pulled away from the switch 18 just prior to the polymer solidifying but after the switch 18 has been set in position, thereby allowing the polymer to fill the space left by the removed holding pins to complete the encapsulation of the switch 18.

Figure 6:
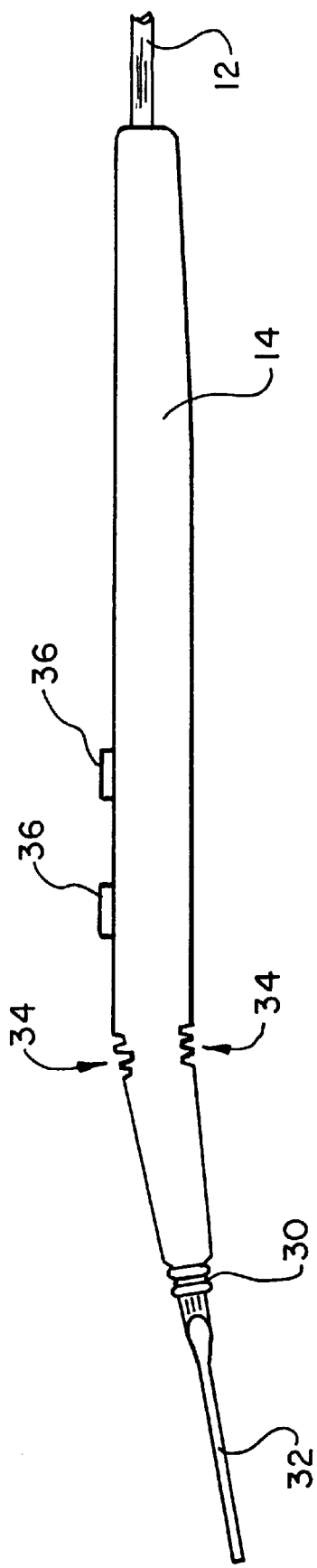
FIG. 6 is a side view of the electrosurgical pencil of FIGS. 1 and 2 in a bent position.
Figure 5:
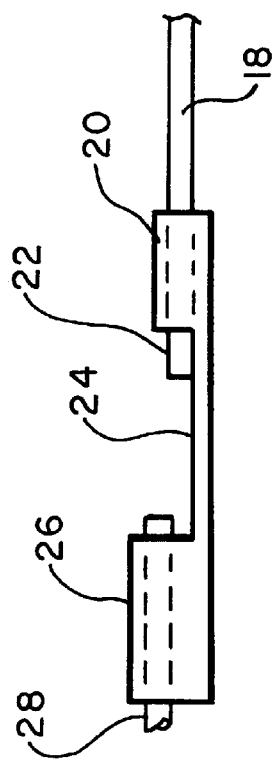
FIG. 5 is a side view of the collet shown in FIG. 4.

The relief grooves 34 overlay the flat portion 24 and provide for the bending of the pencil housing 14 of the pencil 10. The relief grooves 34 more readily allow the pencil housing 14 to flex about an axis running parallel with the grooves 34. The plane of pivoting is substantially the plane illustrated in FIG. 1. Additionally, the flat portion 24 of the metal collet allows the pencil housing 14 to maintain a desired bent configuration of the flexible pencil housing 14. FIG. 6 illustrates the pencil 10 moved to a bent, operative position. It would be possible to bend the pencil 10 without any grooves 34, particularly in a foot controlled pencil 10 where a thinner pencil housing 14 is possible. However, the grooves 34 make it easier to bend the pencil 10. The grooves also localize the bending of the pencil 10 at a position over the flat portion 24 of the collet and further serve as visual indicia to the user as to where the bending should be positioned.

It would be possible to have relief grooves 34 encircle the pencil housing 14 and replace the flat portion 24 with a wire-type member bendable in all directions. However, this alternative configuration is not believed to be necessary due to the rotation of the blade electrode within the socket 26. Consequently, the combination of the rotation of the blade electrode and the pivoting of the pencil housing 14 about the relief grooves 34 in the plane parallel to FIG. 1 combine to allow the blade 32 of the present invention to be orientated in substantially any configuration. This bendable pencil 10 prevents the operator from needing to bend the blade 32 itself which, as discussed above, can be dangerous and can compromise the sterile nature of the blade 32.

In addition to providing the bendable feature of the present invention, the flexible elastomeric polymer forming the pencil housing 14 is more easily gripped by the user and provides a better tactile response in the user's hand than the rigid plastic of the prior art. Additionally, the pencil housing 14 has a smooth surface texture which offers a non-slip surface with the user's glove. The rigid body of the switch 18 provides the needed rigidity to the main portion of the pencil 10. The rigid body of the switch 18 does not permit easy bending or flexing in the portions of the pencil housing 14 encapsulating the switch 18.

As discussed above, the rigid thermoplastic buttons 36 are assembled on the top of the pencil housing 14. The buttons are positioned into an undercut in the recess 38 shown in FIG. 3. Furthermore, because the pencil housing is formed as an elastomeric polymer, the undercut of recess 38 can be formed by a simple injection mold tool. The undercut in the recess 38 holds the button 36 in place while still allowing the up and down movement needed to actuate the dome switch 40.

The switch 18 of the pencil 10 is spaced from the cable receiving end of the pencil housing 14 as illustrated in FIGS. 1 and 2. Additionally, the pencil housing 14 preferably tapers down toward the cable 12. This configuration allows for a certain amount of flex within the pencil housing 14, providing bend relief for the cable 12. The bend relief provided to the cable 12 improves the expected life of the pencil 10 by preventing breakage of the leads 16 in the cable 12 due to high stress concentrations (i.e., wire fatigue). This bend relief for the cable is not present in the rigid pencil housing of the prior art.

Furthermore, the elastomeric encapsulation about the cable of the pencil housing 14 offers inherent stress relief to the cable 12. The cable jacket material is generally similar to the material of the pencil housing 14. The hot polymer forming the pencil housing 14 during the insert molding process creates a thermal bond with the outer cable jacket of the cable 12 providing for a homogenous connection and resulting in a corresponding strain relief.

The electrosurgical pencil 10 of the present invention can be easily designed as a foot controlled pencil without substantially changing the details thereof. For a foot controlled pencil, the buttons 36, recess 38, dome switches 40 and membrane 42 would not be present. Additionally, the switch 18 would be replaced with a rigid body member of substantially the same or thinner shape whereas in the pencil 10 the switch 18 provides the electrical connection between the cable 12 and the attachment end 20 of the metal collet. The body member will place the cable 12 in electrical contact with the attachment end 20 of the metal collet, whereas in the pencil 10 the switch 18 provides the electrical connection between the cable 12 and the attachment end 20 of the metal collet. Additionally, in the foot controlled pencil, an appropriate remotely located controller, typically operated by the user's foot, would be coupled to the cable 12 or possibly to the electrosurgical generator.

It will be obvious to those of ordinary skill in the art that various modifications and changes may be made to the present invention without departing from the spirit and scope thereof. Consequently, the scope of the present invention is intended to be defined by the following claims.

What is claimed is:

1. An electrosurgical pencil for delivering high frequency cutting and coagulation signals from an electrosurgical generator, said pencil comprising:

a flexible, elongated integral, one piece pencil housing having a cable receiving end, a blade electrode receiving end opposed from said cable receiving end, and a means for permitting bending of said pencil housing between said cable receiving end and said blade electrode receiving end;

a cable extending from said cable receiving end of said housing and adapted to be attached to said electrosurgical generator, wherein said housing is thermally bonded to said cable; and an electrical connecting means in said housing extending and attached to said cable and extending to said blade electrode receiving end.

2. The electrosurgical pencil of claim 1 wherein said pencil housing is formed of an elastomeric polymer.

3. An electrosurgical pencil for delivering high frequency cutting and coagulation signals from an electrosurgical generator, said pencil comprising:

a flexible, elongated integral, one piece pencil housing formed of an elastomeric polymer, said housing having a cable receiving end, a blade electrode receiving end opposed from said cable receiving end, and a means for permitting bending of said pencil housing between said cable receiving end and said blade electrode receiving end, wherein said means for permitting bending includes a plurality of relief grooves in said housing;

a cable extending from said cable receiving end of said housing and adapted to be attached to said electrosurgical gnerator; and an electrical connecting means in said housing extending and attached to said cable and extending to said blade electrode receiving end.

4. The electrosurgical pencil of claim 3 wherein said relief grooves are positioned on opposite sides of said pencil.

5. The electrosurgical pencil of claim 1 further including means for retaining a bent position of said pencil housing.

6. An electrosurgical pencil for delivering high frequency cutting and coagulation signals from an electrosurgical generator, said pencil comprising:

a flexible, elongated integral, one piece pencil housing having a cable receiving end, a blade electrode receiving end opposed from said cable receiving end, and a means for permitting bending of said pencil housing between said cable receiving end and said blade electrode receiving end;

a cable extending from said cable receiving end of said housing and adapted to be attached to said electrosurgical generator;

an electrical connecting means in said housing extending and attached to said cable and extending to said blade electrode receiving end; and a means for retaining a bent Position of pencil housing, wherein said means for retaining a bent position of said pencil housing includes a metal collet positioned within said pencil housing, wherein said metal collet is bendable with said pencil housing and said metal collet maintains a bent position of said pencil housing.

7. The electrosurgical pencil of claim 6 wherein said metal collet includes a bendable flat portion and a round blade electrode receiving socket attached to said flat portion for rotatably receiving a blade electrode therein through said blade electrode receiving end.

8. The electrosurgical pencil of claim 7 further including a cable extending into said cable receiving end wherein said housing is hermetically sealed around said flat portion of said metal collet and hermetically sealed around said cable at said cable receiving end.

9. The electrosurgical pencil of claim 8 wherein said housing is substantially solid between said flat portion of said metal collet and said cable receiving end.

10. The electrosurgical pencil of claim 9 wherein said electrical connecting means includes a manually actuated switch embedded within said pencil housing between said metal collet and said cable with said metal collet and said cable attached to said switch.

11. The electrosurgical pencil of claim 10 wherein said switch is spaced from said cable receiving end and wherein said pencil housing tapers from said switch to said cable receiving end.

12. The electrosurgical pencil of claim 10 further including at least one button on said pencil housing, each said button overlaying a depressible activation member on said switch, and including an encapsulating membrane over said activation member between said button and said activation member.

13. The electrosurgical pencil of claim 7 wherein said blade electrode receiving end is spaced from said blade electrode receiving socket of said metal collet, said blade electrode receiving end having a blade electrode engaging aperture extending to said blade electrode receiving socket and adapted to frictionally engage at least a portion of a blade electrode.

14. An electrosurgical pencil for delivering high frequency cutting and coagulation signals from an electrosurgical generator, said pencil comprising:

an elongated elastomeric pencil housing having a first end and opposed second end;

a cable having a first end attachable to an electrosurgical generator and a second end opposed from the first end and extending into said first end of said pencil housing;

an electrically conductive collet positioned at least partially within said pencil housing and electrically coupled to said cable; and a blade electrode attached to said collet and extending from said second end of said pencil housing, wherein said elastomeric pencil housing is sealed to and around a portion of said collet and sealed by thermal bonding to and around a portion of said cable forming a substantially solid hermetically sealed one piece, integral pencil housing therebetween.

15. The electrosurgical pencil of claim 14, wherein said collet includes a flat portion and a round blade electrode receiving socket attached to said flat portion for rotatably receiving said blade electrode therein through said second end of said pencil housing, and wherein said elastomeric pencil housing is sealed around said flat portion of said collet.

16. The electrosurgical pencil of claim 15 further including a plurality of parallel relief grooves on opposite sides of said pencil housing overlaying said flat portion of said metal collet, wherein said relief grooves permit bending of said pencil housing and said flat portion retains said pencil housing in said bent position.

17. The electrosurgical pencil of claim 14 further including a manually actuated switch embedded within said pencil housing between said collet and said cable with said collet and said cable attached to said switch, and wherein said switch includes a rigid switch body.

18. The electrosurgical pencil of claim 17 wherein said switch body is spaced from said first end of said pencil housing and wherein said pencil housing tapers from said switch body to said first end.

19. The electrosurgical pencil of claim 17 wherein said collet includes a flat portion and a round blade electrode receiving socket attached to said flat portion for rotatably receiving said blade electrode therein through said second end of said pencil housing, and wherein said elastomeric pencil housing is sealed around said flat portion of said collet, further including a plurality of parallel relief grooves on opposite sides of said pencil housing overlaying said flat portion of said metal collet, wherein said relief grooves permit bending of said pencil housing and said flat portion retains said pencil housing in said bent position.

* * * * *